United States Patent [19]

Hoegnelid et al.

[11] Patent Number: 5,458,630
[45] Date of Patent: Oct. 17, 1995

[54] MEDICAL ELECTRODE DEVICE HAVING A NON-GASEOUS FLUID CONDUCTOR

[75] Inventors: Kurt Hoegnelid, Vaesterhaninge; Heinz Neubauer, Jaerfaella; Jens Wolf, Johanneshov, all of Sweden

[73] Assignee: Pacesetter AB, Solna, Sweden

[21] Appl. No.: 226,337

[22] Filed: Apr. 12, 1994

[30] Foreign Application Priority Data

Apr. 22, 1993 [SE] Sweden .................................... 9301346

[51] Int. Cl.$^6$ ........................................................ A61N 1/04
[52] U.S. Cl. ........................................................ 607/116
[58] Field of Search ............................ 607/115, 116, 607/119, 120, 121, 122, 129

[56] References Cited

U.S. PATENT DOCUMENTS 3,412,198  3/1965  Wallis .
3,476,116  11/1969  Parsonnet et al. .................. 607/129
3,590,810  7/1971  Kopecky ............................. 607/129
3,884,243  5/1975  Cywinski .
4,058,116  11/1977  Bucalo ............................... 607/116
5,099,855  3/1992  Yount .
5,601,519  8/1971  Wanner et al. .

FOREIGN PATENT DOCUMENTS

0057450  8/1982  European Pat. Off. .............. 607/121
0057451  8/1982  European Pat. Off. .............. 607/121
0311643  8/1971  U.S.S.R. ............................. 607/122

Primary Examiner—William E. Kamm
Attorney, Agent, or Firm—Hill, Steadman & Simpson

[57] ABSTRACT

A medical electrode device of the type suitable for delivering therapeutic electrical energy in vivo to tissue from an implanted pulse generator, includes a sleeve containing a conductor which is a non-metallic, non-gaseous fluid conductor. The non-gaseous, non-metallic fluid conductor may be a conductive gel or an electrolytic liquid.

23 Claims, 7 Drawing Sheets

MEDICAL ELECTRODE DEVICE HAVING A NON-GASEOUS FLUID CONDUCTOR

BACKGROUND OF THE INVENTION

1. Field of the Invention

The present invention is directed a medical electrode of the type having an insulating sleeve containing at least one electrical conductor, the conductor providing an electrical connection between a pulse generator at a proximal end of the electrode device and an electrode surface of the electrode device disposed remote from the proximal end.

2. Description of the Prior Art

Electrode devices of the type generally described above are employed for connecting, for example, a pacemaker or a defibrillator to cardiac tissue in order to sense the functioning of the heart, or to delivery therapeutic electrical energy in vivo to the heart. Generally, known electrode devices are composed of one or more helically wound metal wire conductors running from a contact at the proximal end, connected to the implantable pacemaker or defibrillator, and to an electrode surface disposed at or near the heart. The electrode surface may, for example, be in the form of a relatively small pacing electrode, a larger intracardiac defibrillation electrode, or an epicardiac patch electrode. The known electrode devices can be equipped with different types of sensors which are connected, via a metallic conductor, to the pacemaker or defibrillator.

Because the heart is in constant motion, electrode devices connected to or near the heart are constantly exposed to changes in load and stress. One or more of the metallic conductor wires can fracture, thereby breaking the electrical connection between the electrode surface or a sensor and the contact at the proximal end. If a plurality of metallic wires, electrically insulated from one another, are used, the insulation may sustain abrasion damage caused by the constantly shifting load, resulting in a short-circuit. Additionally, fabrication of the electrode device becomes more complex as the number of incorporated components increases, such as when a plurality of electrode surfaces and sensors must to be connected to single electrode device.

SUMMARY OF THE INVENTION

It is an object of the present invention to provide an electrode device of the type generally described above which is capable of reliably and safely connecting the contact of an implantable pulse generator to electrode surfaces carried by the electrode device, or connecting sensors to the aforementioned contact, without the risk of fractures, short-circuits or the like.

It is a further object of the present invention to provide such an electrode device wherein the number of components can be reduced without any reduction in the number of functions which can be performed by the electrode device.

The above objects are achieved in accordance with the principles of the present invention in a medical electrode device containing an electrical conductor consisting of a non-gaseous, non-metallic fluid.

A non-gaseous, non-metallic fluid conductor is completely reliable as a carrier of energy and signals between the contact and the electrode surface or a sensor. A non-gaseous fluid conductor can withstand an infinite number of load changes without any break occurring, and a thin layer of insulation is sufficient to prevent short-circuits, because a non-gaseous fluid conductor imposes less stressful abrasion loads on the insulation than does a solid conductor.

In a further embodiment of the invention, the insulating sleeve may have an interior channel therein extending between the contact for the pulse generator and the electrode surface, the interior channel being filled with an electrically conductive gel which forms the non-gaseous, non-metallic fluid electrical conductor.

Fabrication of the electrode device of this embodiment is simpler, because the interior channel in the sleeve need only be filled with the fluid gel, and therefore it is not necessary to form the sleeve around a conductor, if the conductor is formed first, nor to thread a conductor through the sleeve, if the sleeve is formed first.

If the electrode device is intended for use in a defibrillation system, in which case the electrode surface will be in the form of one of more patches attached to or applied near the heart, it is preferable for the distal end of the electrode device to include a first, conductive elastic plate and a second, elastic plate joined at the edges, thereby forming a cavity between the first and second plates. The cavity is also filled with a non-gaseous fluid conductor, such an electrically conductive gel, and the electrically conductive elastic first plate and the electrically conductive gel are electrically connected to the non-gaseous fluid electrical conductor contained within the sleeve, so that the conductive plate forms the electrode surface.

This embodiment produces a patch electrode which is supple and compliant. When the electrode surface is, for example, applied directly to the heart, the gel will smoothly conform to an comply with heart movements, in contrast to patches employing, for example, metallic wires.

If an electrically conductive gel is employed as the non-gaseous, non-metallic fluid conductor, the electrically conductive gel preferably consists of a doped polymer gel or a hydrophilic gel. If a doped polymer gel is employed, the gel can be doped with a metallic powder, a salt or powdered carbon.

As an alternative to the use of an electrically conductive gel as the non-gaseous, non-metallic fluid conductor, the interior channel in the insulating sleeve may be filled with an electrolyte which, in use, will be a liquid electrolyte. The use of an electrolyte is particularly appropriate if the electrode device is intended to perform sensing functions.

In the embodiment employing an electrolyte as the non-gaseous fluid conductor, the interior channel of the insulating sleeve is preferably filled at the time of fabrication of the sleeve with undissolved ions. When the device is implanted in the body, the interior channel will become filled with body fluid, which diffuses into the interior channel through the sleeve. The undissolved ions previously contained in the channel prior to implantation will then form a solution with the incoming fluid, thereby resulting in a liquid electrolyte in the channel. This process occurs within a short time after implantation, and is generally completed within a few days.

Alternatively, the electrode surface can be made of an ion-transporting (ion exchange) material.

If the electrode surface is made from an ion-transporting material, no undissolved ions will be needed during fabrication. The electrolyte in the interior channel will be formed by the migration of ions through the ion-transporting material.

In a further embodiment of the invention, the electrode device may include at least one additional electrical conductor for providing an electrical path between at least one additional contact at the proximal end and at least one additional electrode surface.

In principle, the electrode device of the invention can encompass an unlimited number of conductors. If more than one conductor is present, the plurality of conductors can comprise a combination of respective solid, metallic conductors and non-gaseous fluid conductors. If, for example, high energies must be transferred, as in the emission of a defibrillation pulse, an arrangement of solid metallic conductors or a combination of solid, metallic conductors and non-gaseous fluid conductors may be appropriate. The electrode device, may, however, exclusively contain non-gaseous fluid conductors.

Combinations of the above embodiments can also be employed. For example, the electrode device may include a conventional, metallic wire conductor extending between the proximal end contact and the electrode surface of the electrode device, with the electrode surface being constructed as described above by means of a first conductive elastic plate and a second elastic plate joined at the edges, with the cavity therebetween being filled with a non-gaseous fluid conductor such as electrically conductive gel. The electrically conductive elastic plate and the conductive gel are then electrically connected to the metallic electrical conductor, with the conductive plate forming the electrode surface.

DESCRIPTION OF THE PREFERRED EMBODIMENTS

Figure 1:
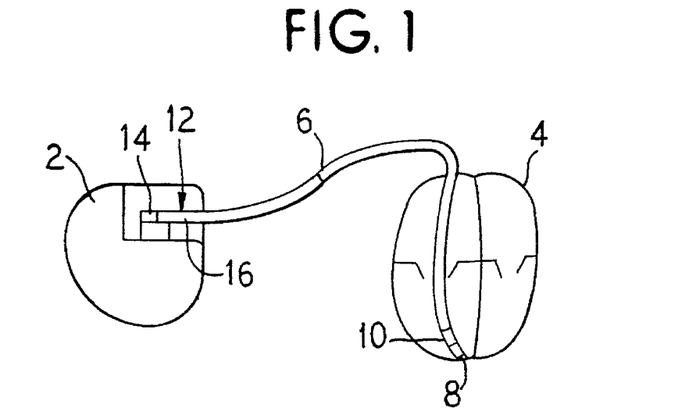
FIG. 1 shows an implantable pacing system employing an electrode device constructed in accordance with the principles of the present invention.

A pacemaker 2 is shown in FIG. 1 connected in vivo to a heart 4 by an electrode device 6. The electrode device 6 is a VVI device, i.e., it has a tip electrode 8 placed in the right ventricle to stimulate the heart 4, and a ring electrode 10 to sense cardiac signals in the ventricle. The electrode device 6 also has a contact terminal 12 having a first contact surface 15 connected to the tip electrode 8 and to pacing electronics contained within the pacemaker 2, and a second contact surface 16 connected to the ring electrode 10 and to the pacing electronics.

Figure 8:
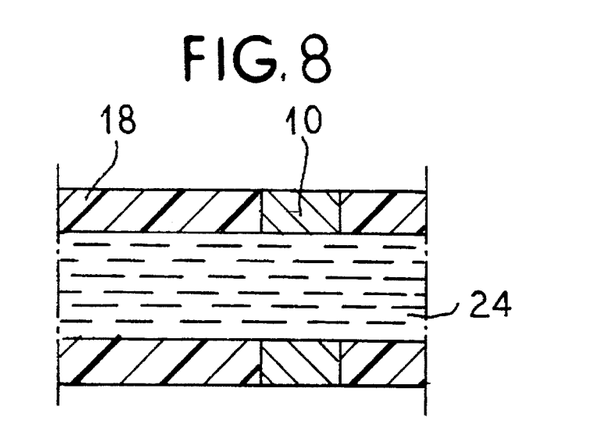
FIG. 8 is a sectional view of a basic embodiment of an electrode device constructed in accordance with the principles of the present invention.

As shown in FIG. 8, the electrode device is formed by an insulating sleeve 18 having an interior channel. Although only a portion of the electrode device is shown in section in FIG. 8, the interior channel extends completely between the contact terminal 12 and the opposite end at which the ring electrode 10 and the tip electrode 8 are disposed. The interior channel is completely filled with a non-gaseous, non-metallic conductor 24, which electrically connects the contact terminal 12 to the ring electrode 10. FIG. 8 schematically illustrates the basic components of the electrode device of the invention, and it will be understood that a further conductive path, shown in the various embodiments below, is provided for connection to the tip electrode 8.

Figure 2:
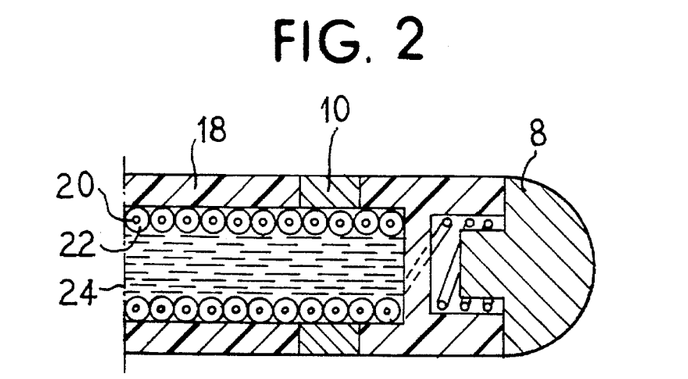
FIG. 2 is a sectional view of an embodiment of an electrode device constructed in accordance with the principles of the present invention.
Figure 3:
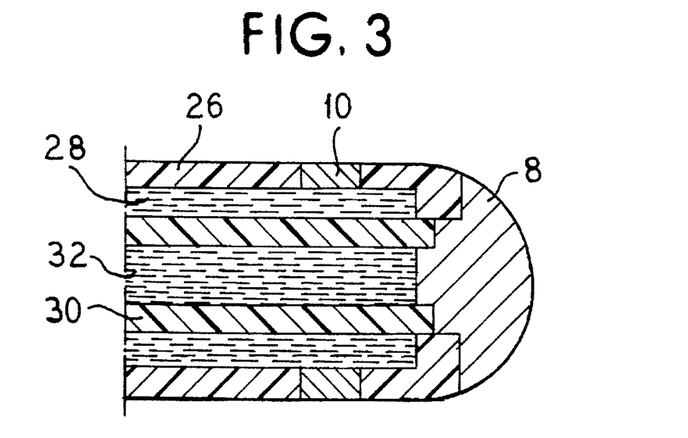
FIG. 3 is a sectional view of a further embodiment of the electrode device constructed in accordance with the principles of the present invention.

A section one such embodiment of the electrode device is shown in FIG. 2. The electrode device of FIG. 2 includes a metallic conductor 20 which is helically arranged in an interior channel of an insulating sleeve 18. The metallic conductor 20 has a coating of insulation 22 so as to insulate the metallic conductor 20 from the electrolyte 24 which fills the interior channel in the insulating sleeve 18. In all embodiments ring electrode 10 is an integral part of the insulating sleeve 18. The ring electrode 10 may be, for example, a platinum electrode, or a membrane made of a conductive material, in contact with the electrolyte 24 and the surrounding body tissue in order to receive and transmit electrical signals to and from the pacemaker An alternative version of the electrode device is shown in FIG. 3. In this version, the electrode device is enclosed by a first insulating sleeve 26, and an insulating tube 30 is located inside the sleeve 26. A first non-gaseous, non-metallic fluid conductor 28 is disposed in the space between the tube 30 and the sleeve 26. The non-gaseous, non-metallic fluid conductor 28 may be an electrolyte or a conductive gel.

A second, non-gaseous, non-metallic fluid conductor 32 is located inside the insulating tube 30 for connecting the tip electrode 8 to the pacemaker 2. The second non-gaseous, non-metallic fluid conductor 32 may be a conductive gel, for example, a doped polymer gel. Again, the ring electrode 10 may be a metallic ring, or a membrane made of conductive material.

Figure 4:
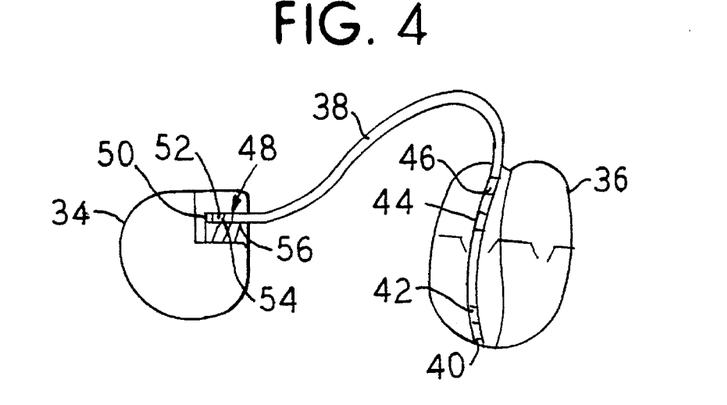
FIG. 4 shows an implantable pacing system employing another embodiment of an electrode device constructed in accordance with the principles of the present invention.

A further embodiment of the electrode device according to the invention is shown in FIG. 4. In the embodiment, a pacemaker 34 is connected to a heart 36 by an electrode device 38. The electrode device 38 is a VDD electrode, and has a tip electrode 40 disposed in the right ventricle to stimulate cardiac tissue, a first ring electrode 42 for sensing cardiac signals in the ventricle, and second and third ring electrodes 44 and 46 for sensing atrial activity in the heart 36. The electrode device 38 is detachably connected to the pacemaker 34 by a contact terminal 48. The contact terminal 48 has a first contact surface 50 which is connected to the tip electrode 40, a second contact surface 52 connected to the first ring electrode 42, a third contact surface 54 connected to the second ring electrode 44 and a fourth contact surface 56 connected to the third ring electrode 46.

Figure 5A:
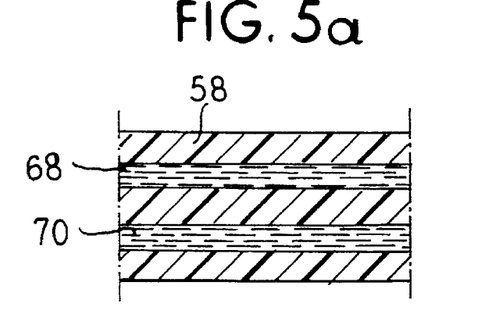
FIGS. 5a and 5b show details of an exemplary structure of the embodiment of FIG. 4.
Figure 5B:
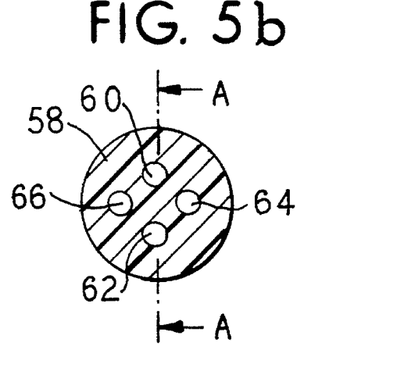

FIG. 5a shows a longitudinal cross-section of the electrode device 38 and FIG. 5b shows a cross-section of the electrode device 38 taken perpendicularly to its longitudinal axis. The electrode device 38 includes an insulating sleeve 58 having four interior channels 60, 62, 64 and 66 therein. The interior channels 60, 62, 64 and 66, when filled with a non-gaseous, non-metallic fluid conductor, respectively connect the tip electrode 40, the first ring electrode 42, the second ring electrode 44 and the third ring electrode 46 (FIG. 4) to the pacemaker 34 via the aforementioned contact surfaces of the contact terminal 48. The interior channel 60, which connects the tip electrode 40 to the first contact surface 50 may be filled with an electrically conductive gel 68, and the other interior channels 62, 64 and 66 may be filled with a conductive gel or an electrolyte.

Figure 6:
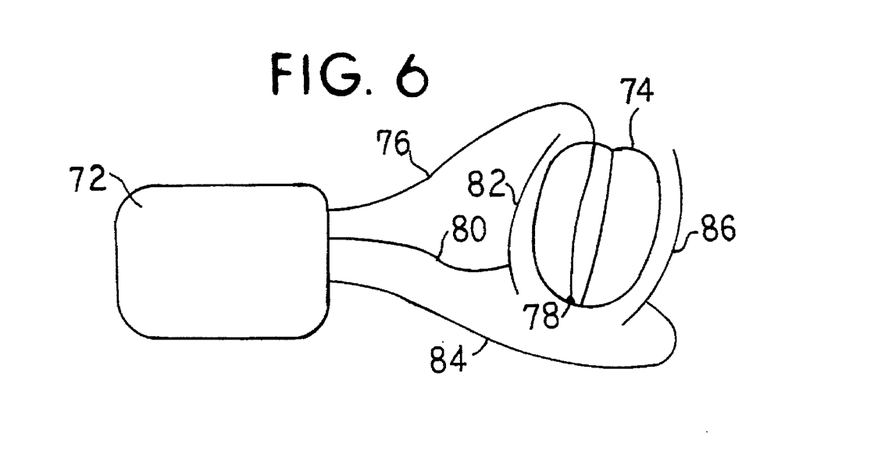
FIG. 6 shows an implantable defibrillation system employing another embodiment of an electrode device constructed in accordance with the principles of the present invention.

A defibrillator 72 is shown in FIG. 6 connected in vivo to a heart 74 via a first electrode device 76 having a tip electrode 78 affixed in the right ventricle of the heart 74. The defibrillator 72 can, via the first electrode device 76, supply the heart with the same electrical therapy as a pacemaker. The first electrode device 76 has only one electrical conductor from the defibrillator 72 to the tip electrode 78. This electrical conductor may be a non-gaseous, non-metallic fluid conductor, such an electrically conductive gel, as in any of the previously described embodiments. In order to defibrillate the heart 74, the defibrillator 72 is connected to a second electrode device 80 and to a third electrode device 84. The second electrode device 80 has a first defibrillation electrode 82 designed to be placed directly on or near the heart 74. The third electrode device 84 has a second defibrillation electrode 86 which, corresponding to the first defibrillation electrode 82, can be placed directly on or near the heart 74. A defibrillation pulse from the defibrillator 72 is delivered across the first defibrillation electrode 82 and the second defibrillation electrode 86, so that the pulse passes through the heart 74. The second electrode device 80 and the third electrode device 84 may have solid, metallic conductors, or non-metallic, non-gaseous fluid conductors.

Figure 7A:
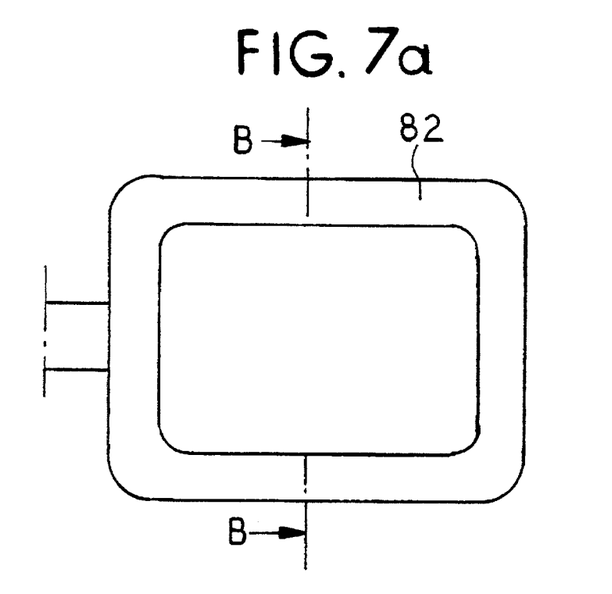
FIGS. 7a and 7b respectively illustrate the details of an embodiment of a defibrillation electrode constructed in accordance with the principles of the present invention.
Figure 7B:
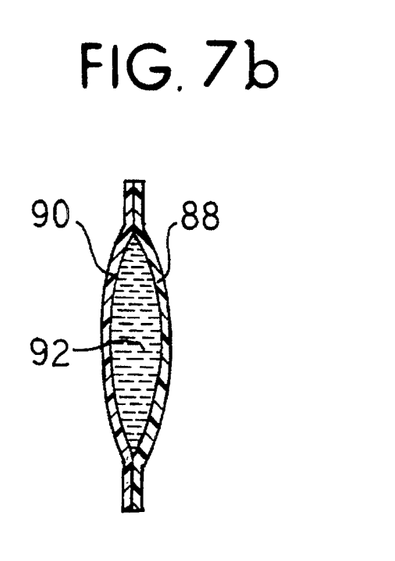

FIGS. 7a and 7b show the first defibrillation electrode 82 in greater detail. The first defibrillation electrode 82 has a first electrode plate 88, made from a conductive, elastic material, and a second electrode plate 90, which also is made from an elastic material, which can be conductive or insulating. The two electrode plates 88 and 90 are joined at their edges, thereby forming a cavity which is filled with a non-gaseous fluid conductor 92, such as an electrically conductive gel. The first defibrillation electrode 82 is applied to the heart 74 with the conductive plate 88 on or facing the heart 74. The gel-filled cavity makes the first defibrillation electrode 82 supple and adaptable to the movements of the heart 74.

Figure 9:
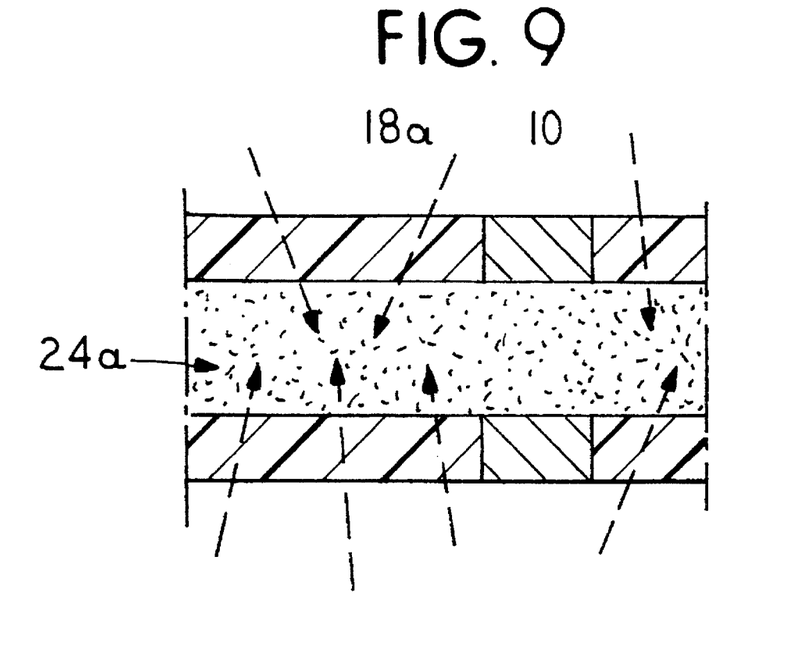
FIG. 9 is a sectional view showing an embodiment of an electrode device constructed in accordance with the principles of the present invention employing a dry electrolyte and a body fluid-defusing sleeve.

An embodiment employing an electrolyte as the non-gaseous, non-metallic fluid conductor is shown in FIG. 9, wherein the insulating sleeve 18a is formed of material through which body fluids can diffuse. The insulating sleeve 18a is preferably filled at the time of fabrication of the sleeve 18a with dry electrolyte (undissolved ions) 24a. When the sleeve 18a is implanted in the body, the interior channel will become filled with body fluid, which diffuses into the interior channel through the sleeve 18a as schematically indicated by the dashed arrows. The undissolved ions contained in the channel prior to implantation will then form a solution with the incoming fluid, thereby resulting in a liquid electrolyte in the channel. This process occurs within a short time after implantation, and is generally completed within a few days.

Figure 10:
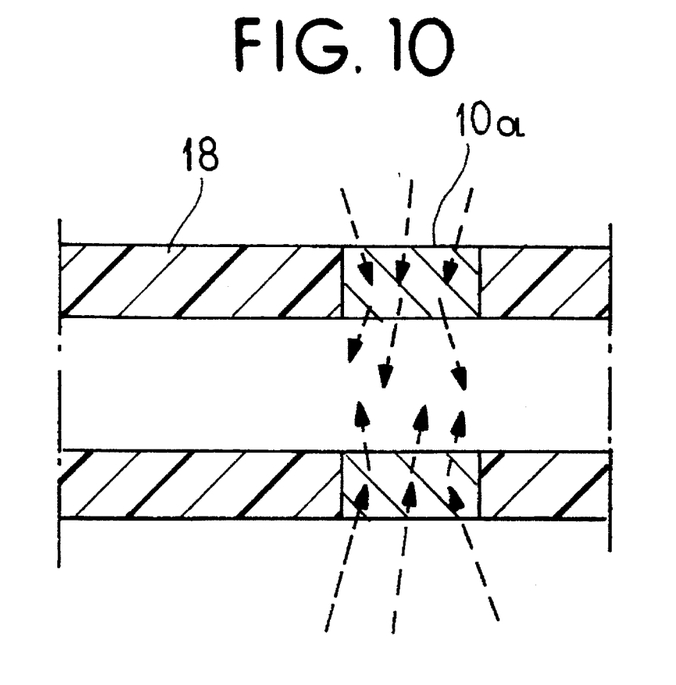
FIG. 10 is a sectional view of an embodiment of an electrode device constructed in accordance with the principles of the present invention employing an electrode surface of ion-transporting material.

In the embodiment shown in FIG. 10, the electrode surface 10a is made of an ion-transporting (ion exchange) material. In this embodiment, no undissolved ions are needed during fabrication. The electrolyte in the interior channel is formed after implantation by the migration of ions through the ion transporting material, as indicated by the sets of dashed arrows indicating ions in body fluid entering into the electrode surface 10a and an ion transportation or ion exchange taking place in the electrode surface 10a, resulting in ions entering into the interior channel of the sleeve 18.

Figure 11:
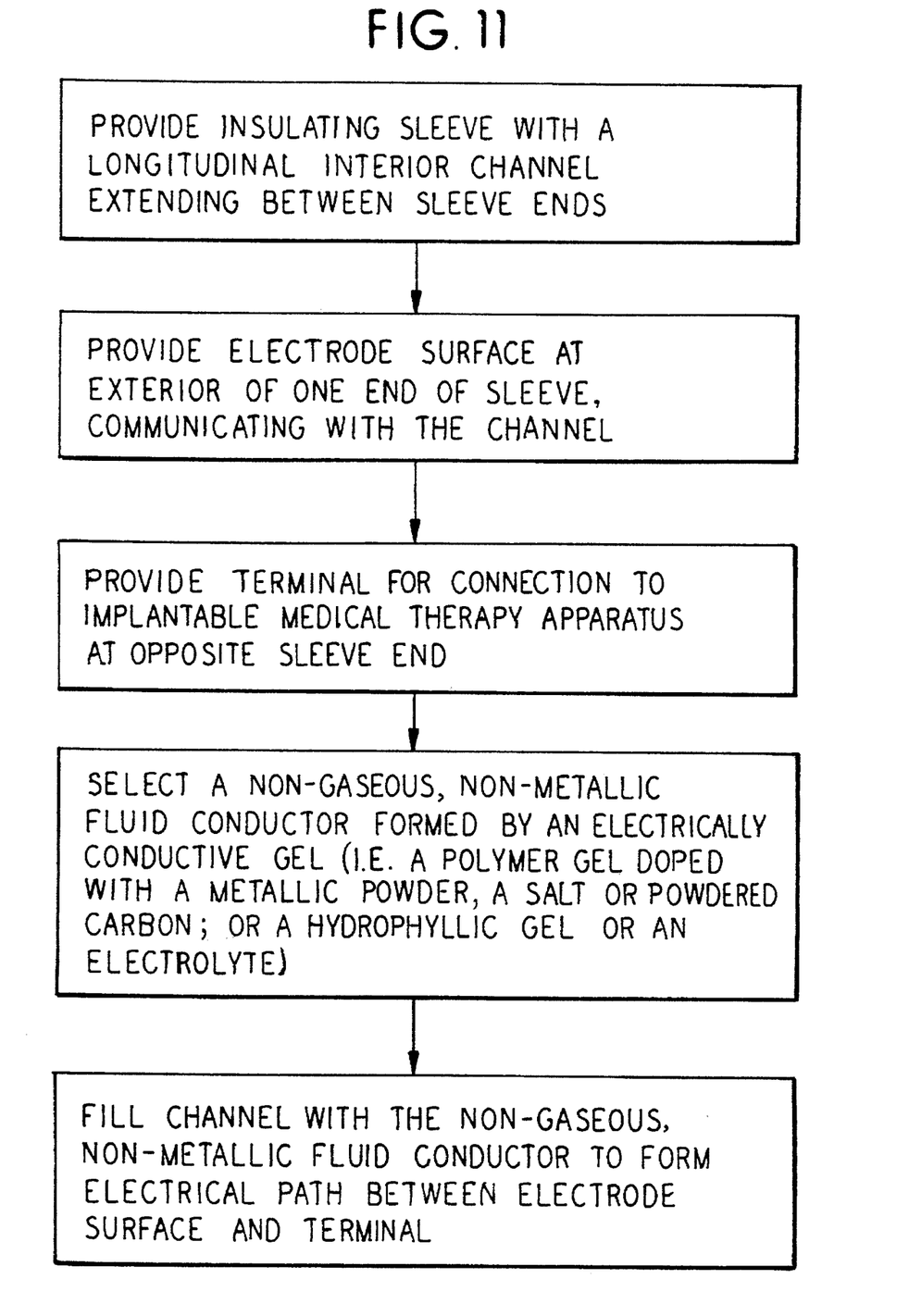
FIG. 11 is a flowchart showing the basic steps for producing an in vivo electrical connection employing any of the embodiments shown in FIGS. 1–8.
Figure 12:
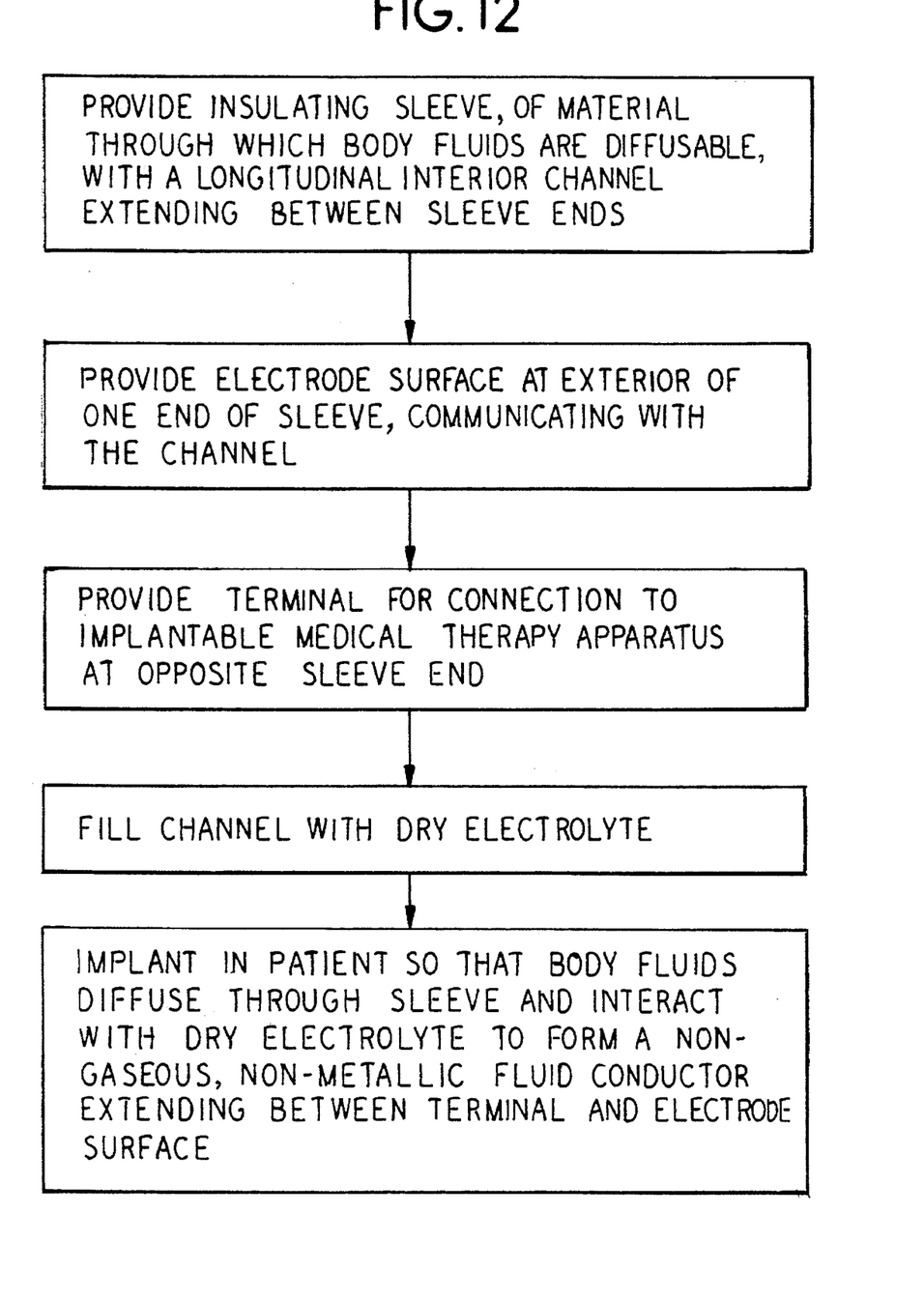
FIG. 12 is a flowchart showing the basic steps in a method for producing an in vivo electrical connection employing the embodiment shown in FIG. 9.
Figure 13:
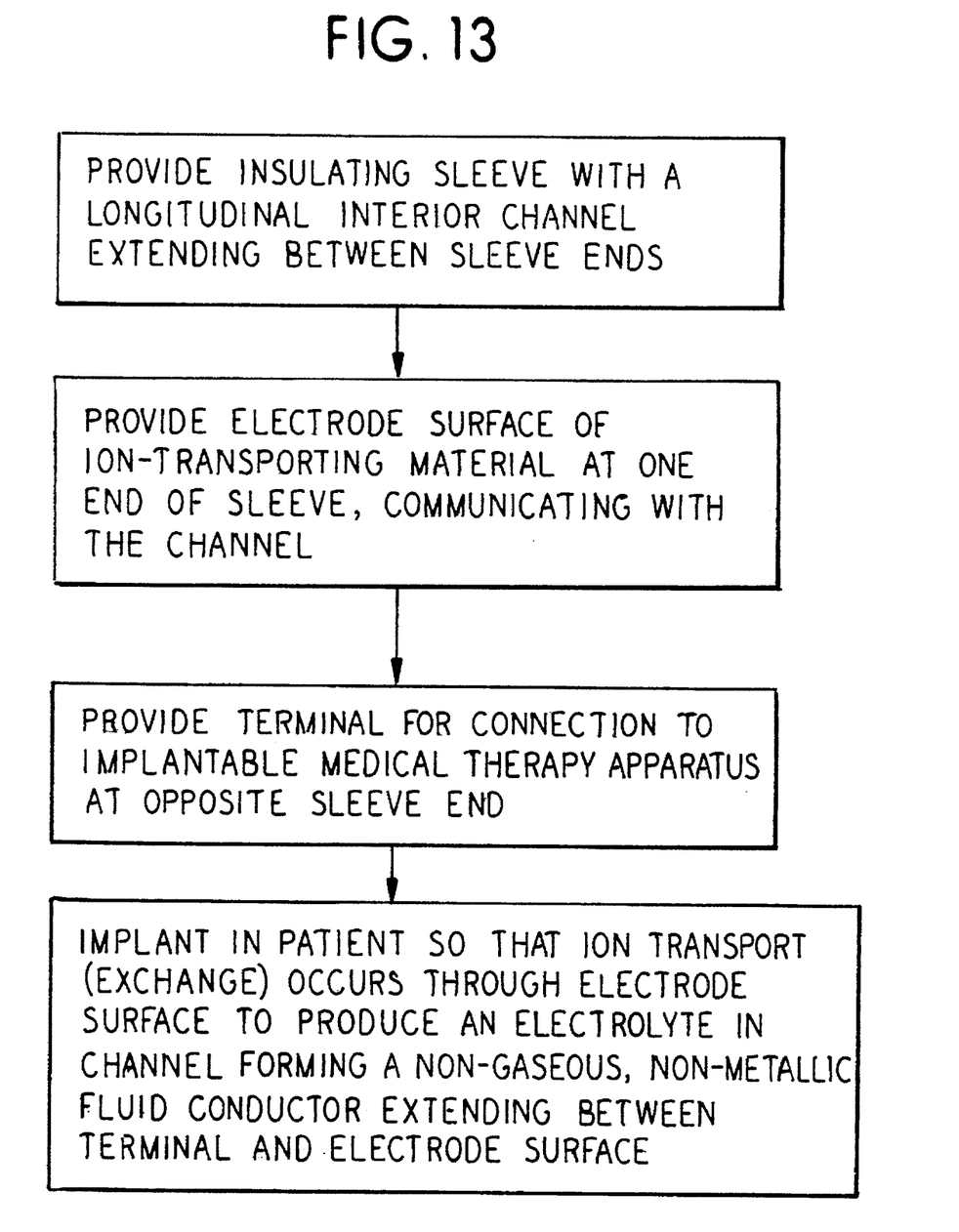
FIG. 13 is a flowchart showing the basic steps for producing an in vivo electrical connection employing the embodiment of FIG. 10.

FIGS. 11, 12 and 13 show the basic method steps for producing an electrical connection between a, preferably implanted, medical therapy apparatus of the type shown in FIGS. 1, 4 and 6, and an in vivo therapy site located at the distal end of the electrode device. The basic method steps shown in FIG. 11 apply to the embodiments shown in FIGS. 1 through 8, the basic steps of FIG. 12 apply to the embodiment shown in FIG. 9, and the basic steps of FIG. 13 apply to the embodiment of FIG. 10.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical electrode device comprising:

an elongated insulating sleeve having a hollow interior channel extending longitudinally along a complete length of said sleeve;

a contact terminal disposed at a first end of said insulating sleeve and connectable to an implantable medical therapy apparatus;

said insulating sleeve having an exposed electrode surface at a second, opposite end of said sleeve; and at least one electrical conductor consisting of non-gaseous, non-metallic fluid in said interior channel extending completely between and electrically connecting said contact terminal and said electrode surface.

2. An electrode device as claimed in claim 1 wherein said non-gaseous, non-metallic conductor comprises an electrically conductive gel.

3. An electrode device as claimed in claim 2 wherein said non-gaseous, non-metallic electrical conductor comprises an electrically conductive gel selected from the group consisting of doped polymer gels.

4. An electrode as claimed in claim 3 wherein said doped polymer gels are selected from the group consisting of gels respectively doped with a metallic powder, a salt or powdered carbon.

5. An electrode device as claimed in claim 2 wherein said electrically conductive gel comprises hydrophilic gel.

6. An electrode device as claimed in claim 1 further comprising, at said second end, a first electrically conductive elastic plate, a second elastic plate, said first and second plates being joined at their edges to form a cavity between said first and second plates, an electrically conductive gel filling said cavity, said first plate and said electrically conductive gel being electrically connected to said non-gaseous, non-metallic fluid conductor, and said first plate forming said electrode surface.

7. An electrode device as claimed in claim 6 wherein said electrically conductive gel is selected from the group consisting of doped polymer gels.

8. An electrode as claimed in claim 7 wherein said doped polymer gels are selected from the group consisting of gels respectively doped with a metallic powder, a salt or powdered carbon.

9. An electrode device as claimed in claim I wherein said non-gaseous, non-metallic fluid conductor comprises an electrolyte.

10. An electrode device as claimed in claim 9 wherein said interior channel is filled prior to implantation with undissolved ions, wherein said insulating sleeve consists of material through which body fluids are diffusible, and wherein said electrolyte is formed by dissolving said ions in body fluid diffused through said insulating sleeve into said interior channel after implantation.

11. An electrode device as claimed in claim 9 wherein said electrode surface consists of an ion-transporting material and wherein said electrolyte is formed by ions in solution transported through said electrode surface.

12. An electrode device as claimed in claim 1 further comprising at least one further electrical conductor and at least one further electrode surface, said further electrical conductor electrically connecting said contact terminal to said further electrode surface.

13. An electrode device as claimed in claim 12 wherein said further electrical conductor consists of non-gaseous, non-metallic fluid.

14. An electrode device as claimed in claim 12 wherein said further electrical conductor consists of metal.

15. An electrode device as claimed in claim 1 wherein said non-gaseous, non-metallic electrical conductor consists of hydrophilic gel.

16. An electrode device comprising:
  an insulating sleeve having an interior channel therein, said interior channel having an inner diameter;
  an insulating tube disposed in said interior channel of said sleeve, said insulating tube having an outer diameter which is smaller than said inner diameter of said interior channel and said insulating sleeve and said insulating tube being substantially coextensive so that an annular channel is formed between said insulating tube and said insulating sleeve, each of said insulating sleeve and said insulating tube having a first end and a second end;
  a contact terminal disposed at said first ends of said insulating tube and said insulating sleeve and connectable to an implantable medical therapy apparatus, and said second end of said insulating sleeve closing said annular channel;
  first and second electrode surfaces disposed at an exterior of said insulating sleeve;
  a first non-gaseous, non-metallic electrical conductor disposed in and extending along a complete length of said annular channel and electrically connecting said contact terminal to said first electrode surface; and
  a second non-gaseous, non-metallic fluid electrical conductor contained inside and extending along a complete length of said insulating tube and electrically connecting said contact terminal and said second electrode surface.

17. A method for producing an electrical connection between a medical therapy apparatus and an in vivo site in a subject comprising the steps of:
  providing an insulating sleeve having a hollow channel therein;
  providing an electrode surface on said insulating sleeve at a first end of said sleeve;
  providing an electrical terminal at a second, opposite end of said sleeve;
  filling said interior channel of said insulating sleeve with a non-gaseous, non-metallic fluid conductor extending completely between said contact terminal and said electrode surface; and
  implanting said insulating sleeve and connecting said terminal to a medical therapy apparatus and disposing said electrode surface at said in vivo site.

18. A method as claimed in claim 17 wherein the step of filling said interior channel of said insulating sleeve with a non-gaseous, non-metallic fluid is further defined by filling said interior channel of said insulating sleeve with an electrically conductive gel.

19. A method as claimed in claim 18 comprising the additional step of selecting said electrically conductive gel from the group consisting of doped polymer gels.

20. A method as claimed in claim 19 comprising the additional step of selecting a doped polymer gel from the group consisting of polymer gels doped with a metallic powder, a salt or powdered carbon.

21. A method as claimed in claim 18 wherein the step of filling said interior of said insulating sleeve with a non-gaseous, non-metallic fluid conductor comprises filling said interior channel of said insulating sleeve with hydrophilic gel.

22. A method as claimed in claim 17 wherein the step of providing an insulating sleeve is further defined by providing an insulating sleeve consisting of material through which body fluids are diffusible, and wherein the step of filling said interior channel of said insulating sleeve with a non-gaseous, non-metallic fluid conductor is further defined by the steps of:
  filling said interior channel of said insulating sleeve with undissolved ions; and
  implanting said insulating sleeve in an environment wherein said insulating sleeve is in contact with body fluids which diffuse through said insulating sleeve anti interact with said undissolved ions to form an electrolyte in said interior channel.

23. A method as claimed in claim 17 wherein the step of providing an electrode surface on said insulating sleeve is further defined by providing an electrode surface consisting of ion-transporting material, and wherein the step of filling said interior channel of said insulating sleeve with a non-gaseous, non-metallic fluid conductor is further defined by the step of:
  implanting said insulating sleeve in an environment containing body fluids, said body fluids transporting ions through said electrode surface to form an electrolyte in said interior channel.

* * * * *